United States Patent
Bonrath et al.

(10) Patent No.: US 8,829,231 B2
(45) Date of Patent: Sep. 9, 2014

(54) PREPARATION OF 4-ACETOXY-2-METHYLBUTANAL BY CATALYTIC CARBON CARBON DOUBLE BOND HYDROGENATION

(75) Inventors: Werner Bonrath, Kaiseraugst (CH); Jan Schütz, Kaiseraugst (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/980,118

(22) PCT Filed: Jan. 16, 2012

(86) PCT No.: PCT/EP2012/050544
§ 371 (c)(1),
(2), (4) Date: Dec. 2, 2013

(87) PCT Pub. No.: WO2012/098067
PCT Pub. Date: Jul. 26, 2012

(65) Prior Publication Data
US 2014/0081042 A1    Mar. 20, 2014

(30) Foreign Application Priority Data
Jan. 19, 2011  (CH) .......................................... 97/11

(51) Int. Cl.
*C07C 67/02*   (2006.01)

(52) U.S. Cl.
USPC .......................................................... 560/266

(58) Field of Classification Search
USPC .......................................................... 560/266
See application file for complete search history.

(56) References Cited

U.S. PATENT DOCUMENTS
3,649,672 A    3/1972    Himmele et al.

FOREIGN PATENT DOCUMENTS
EP    1 174 414    1/2002

OTHER PUBLICATIONS

International Search Report for PCT/EP2012/050544, mailed Jul. 2, 2012.
Byeongno et al., "Regioselective hydroformylation of allyl acetates catalyzed by rhodium-montmorillonite", *Journal of Molecular Catalysis A: Chemical*, vol. 111, 1996, pp. 17-23.

*Primary Examiner* — Jafar Parsa
(74) *Attorney, Agent, or Firm* — Nixon & Vanderhye P.C.

(57) ABSTRACT

The present invention relates to a new way for the production of 4-acetoxy-2-methyl-butanal, wherein a non-acidic catalytic system is used.

16 Claims, No Drawings

PREPARATION OF 4-ACETOXY-2-METHYLBUTANAL BY CATALYTIC CARBON CARBON DOUBLE BOND HYDROGENATION

This application is the U.S. national phase of International Application No. PCT/EP2012/050544 filed 16 Jan. 2012 which designated the U.S. and claims priority to CH Patent Application No. 00097/11 filed 19 Jan. 2011, the entire contents of each of which are hereby incorporated by reference.

The present invention relates to a new way for the production of 4-acetoxy-2-methyl-butanal.

4-acetoxy-2-methyl-butanal, which is the following compound of formula (I)

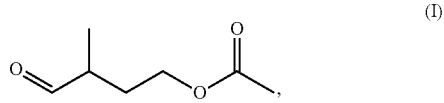

(I)

is an important building block compound for the synthesis of organic compounds such as vitamin A, vitamin E, carotenoids and terpenoids.

Due to the complexness of the synthesis of organic compounds such as vitamin A, vitamin E, carotenoids and terpenoids it is desirable that the building block compounds (intermediates) are synthesized in an efficient manner. There is always a need for improved ways of such syntheses.

Until today, efficient hetero-catalytic selective hydrogenation of compounds containing the functional groups of a $\alpha,\beta$-unsaturated aldehyde and an ester function is not known. Such compounds like those of formula (I) are very prone to saponify under the usual reaction condition.

Surprisingly it was found out that by the choice of the catalytic system a non-acidic catalytic system by-passes the saponification problem.

The present invention relates to a process for the production of 4-acetoxy-2-methyl-butanal, which results in very good yields and selectivity. This process can also be carried at low temperature (room temperature).

Surprisingly this hydrogenation does not work well for similar compounds like citral.

The starting material for this process is 4-acetoxy-2-methyl-2-butenal, which is represented by the following formula (II)

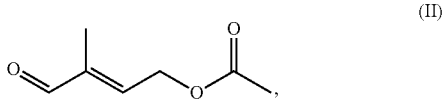

(II)

which is hydrogenated selectively. This means that the carbon-carbon double bond is hydrogenated.

Therefore the present invention relates to a process for the production of 4-acetoxy-2-methyl-butanal which comprises the hydrogenation of 4-acetoxy-2-methyl-2-butenal, wherein the hydrogenation is carried out by using a non-acid catalytic system.

In the context of the present invention the term non-acid catalytic system is defined as follows: An aqueous extract of the catalyst systems used in the process according to the present invention has a pH$\geq$7. Preferably, the aqueous extract has a pH of >7 (=basic catalytic system), more preferred the pH is >7 and <9.

The catalytic system can be a single compound or a mixture of compounds. When a mixture is used, then not all compounds have to have a pH (as an aqueous extract) of $\geq$7, but the mixture has to fulfill this requirement.

The non-acid catalytic system comprises a heterogeneous Pd based catalyst. The catalyst comprises a carrier material on which the Pd is brought on. Such carrier materials are i.e. carbon (preferably in basic form), $CaCO_3$ and $Al_2O_3$ (preferably in basic form). Preferred is the use of a basic carrier.

It is also suitable to add at least one modifier, which is basic. This is essential in those cases wherein the carrier material is not basic. Such a modifier is chosen from the group of inorganic or organic bases. Preferred modifiers are $Na_2CO_3$, Na(acetate), K(acetate), $K_2CO_3$ and $Co(acetate)_2$.

More preferred are non-acidic catalytic systems, which comprise the use of a basic carrier (on which the Pd metal is brought on) without additional basic modifiers. Examples of such more preferred non-acidic catalytic systems are Pd/C (basic carbon), Pd/$CaCO_3$, Pd/$Al_2O_3$ (basic $Al_2O_3$) and Pd,Pb/$CaCO_3$.

The non-acid catalyst system is used in an amount of 0.25 weight-% (wt-%) to 10 wt-%, based on the total weight of 4-acetoxy-2-methyl-2-butenal. Preferably, the catalytic system is used in an amount of 0.5 wt-% to 8 wt-%, based on the total weight of 4-acetoxy-2-methyl-2-butenal.

The process can be carried out at temperature between 0° C. and 100° C. Preferably the process is carried out at temperature between 10° C. and 50° C. It is an advantage that the process according to the present invention can be carried out at low temperature (i.e. at room temperature, 20° C. to 25° C.).

The process is carried out in a polar solvent (or in a mixture of solvents). The polar solvent can be protic or aprotic. Suitable polar solvents do have a polarity of $1\text{-}25\times10^{-30}$ Cm, preferred $4\text{-}18\times10^{-30}$ Cm.

The polarity of the solvents is determined according to commonly known methods. Suitable solvents are alcohols, ethers, esters, ketones, carbonates and lactames. Examples of preferred solvents are $C_1$-$C_6$-alcohols (such as methanol and ethanol) and propylene carbonate.

The process according to the present invention is usually carried out at 0.2 to 20 bar pressure, more preferably at 0.5 to 10 bar.

The isolation of the reaction product of the process according to the present invention is done by using conventional methods. It is also possible that the product of formula (I) is not isolated, but used in situ for further reaction procedures.

The following examples serve to illustrate the invention. All percentages are given in weight percentages and the temperatures are given in ° C.

EXAMPLES

Example 1

In a glass autoclave 4-acetoxy-2-methyl-2-butenal (20.0 g, 140.7 mmol), methanol (200.0 g), palladium on charcoal (1720 mg, 5% palladium), and sodium carbonate (340.0 mg, 3.21 mmol) were added. The closed autoclave was agitated (1000 rpm) at 21° C. for 45 min. The hydrogen pressure was set to 0.5 bar. GC-area % showed a yield of 4-acetoxy-2-methyl-butanal of 95.2% (100.0% conversion).

Example 2

In a glass autoclave 4-acetoxy-2-methyl-2-butenal (1.0 g, 7.03 mmol), methanol (10.0 g), palladium on charcoal (86 mg, 5% palladium), and sodium carbonate (17.0 mg, 0.16 mmol) were added. The closed autoclave was agitated (1000 rpm) at 23° C. for 37. The hydrogen pressure was set to 0.5. GC-area % showed a yield of 4-acetoxy-2-methyl-butanal of 99% (100.0% conversion).

Examples 3 to 6

The following examples have been carried out in analogy to Example 2 (with the exemption that no modifier has been added). The catalytic system always comprises a basis carrier.

TABLE 1

Examples 3 to 6

| Exp. | Cat system | Cat [mg] | Solvent | P [bar] | t [min] | Yield [%] |
|---|---|---|---|---|---|---|
| 3 | 5% Pd/C | 159 | methanol | 0.5 | 8 | 97 |
| 4 | 5% Pd/C | 86 | n-butanol | 10 | 120 | 98 |
| 5 | 5% Pd/C | 86 | propylene-carbonate | 10 | 120 | 97 |
| 6 | 5% Pd/Al$_2$O$_3$ | 86 | methanol | 10 | 120 | 94 |

Examples 7 to 12 (Comparison Examples)

To demonstrate that the process according to the present invention is surprising, the following comparison tests have been made. Instead of using 4-acetoxy-2-methyl-2-butenal as a starting material the structurally similar compound citral (compound of formula (III))

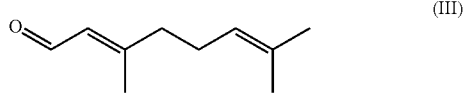

has been used.

The hydrogenated compound, which is obtained, is citronellal (compound of formula (IV))

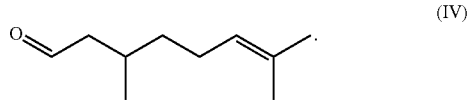

The same reaction conditions have been used as for the process according to the present invention.

TABLE 2

Comparison experiments (hydrogenation of citral) using a non-acid catalytic system comprising a modifier. The catalytic system (incl. modifier) has been added in amount 8.6 wt-% Pd catalyst and 1.7 wt-% basic modifier, based on the total amount of citral, the reaction temperature was 23° C. and the pressure was 10 bar, the reaction time was 60 minutes.

| Exp. | Cat. | Solvent | Yield [%] | Conversion [%] |
|---|---|---|---|---|
| 7 | 5% Pd/C & Na$_2$CO$_3$ | ethanol | 52 | 100 |
| 8 | 5% Pd/C & Na$_2$CO$_3$ | 2-propanol | 42 | 100 |
| 9 | 5% Pd/Al$_2$O$_3$ & Na$_2$CO$_3$ | methanol | 42 | 100 |
| 10 | 5% Pd/C & Na$_2$CO$_3$ | methanol | 57 | 73 |

TABLE 3

Comparison experiments (hydrogenation of citral) using a non-acid catalytic system (with basic carrier and no modifier). The catalytic system has been added in amount of 8.6 wt-%, based on the total amount of citral, the reaction temperature was 23° C. and the pressure was 10 bar, the reaction time was 60 minutes.

| Exp. | Cat. | Solvent | Yield [%] | Conversion [%] |
|---|---|---|---|---|
| 11 | 5% Pd/C | propylene-carbonate | 33 | 100 |
| 12 | 5% Pd/C | n-hexane | 60 | 100 |

The reactions do not lead to the same excellent yields as for the hydrogenation of 4-acetoxy-2-methyl-2-butenal.

The invention claimed is:

1. A process of production of 4-acetoxy-2-methyl-butanal which comprises subjecting 4-acetoxy-2-methyl-2-butenal to hydrogenation in a polar solvent and in the presence of a non-acid catalytic system.

2. The process according to claim 1, wherein the process is carried out in a mixture of polar solvents.

3. The process according to claim 1, wherein the polar solvent is protic or aprotic.

4. The process according to claim 1, wherein the polar solvent has a polarity of $1-25 \times 10^{-30}$ Cm.

5. The process according to claim 1, wherein the polar solvent is at least one selected from the group consisting of alcohols, ethers, esters, ketones, carbonates and lactames.

6. The process according to claim 1 wherein the catalytic system comprises a heterogeneous Pd based catalyst.

7. The process according to claim 1 wherein the catalytic system comprises a basic modifier.

8. The process according to claim 1, wherein the basic modifier is chosen from the group consisting of Na$_2$CO$_3$, Na(acetate), K(acetate), K$_2$CO$_3$ and Co(acetate)$_2$.

9. The process according to claim 5, wherein the catalytic system comprises a basic carrier.

10. The process according to claim 1, wherein the non-acid catalytic system is present in an amount of 0.25 wt-% to 10 wt-%, based on total weight of 4-acetoxy-2-methyl-2-butenal.

11. The process according to claim 1, wherein the process is carried out at a reaction temperature between 0° C. and 100° C.

12. The process according to claim 1, wherein process is carried out at a pressure of 0.2 to 20 bar.

13. The process according to claim 12, wherein the process is carried out at a pressure of 0.5 to 10 bar.

14. The process according to claim 4, wherein the polar solvent has a polarity of $4-18 \times 10^{-30}$ Cm.

15. The process according to claim 10, wherein the non-acid catalytic system is present in an amount of 0.5 wt-% to 8 wt-%, based on the total weight of 4-acetoxy-2-methyl-2-butenal.

16. The process according to claim 11, wherein the process is carried out at a reaction temperature between 10° C. and 50° C.

* * * * *